(12) United States Patent
Eddy et al.

(10) Patent No.: US 12,040,082 B2
(45) Date of Patent: Jul. 16, 2024

(54) USE OF AUDIO DATA FOR MATCHING PATIENTS WITH HEALTHCARE PROVIDERS

(71) Applicant: UnitedHealth Group Incorporated, Minnetonka, MN (US)

(72) Inventors: Meihua S. Eddy, Los Angeles, CA (US); Ronald Matthew Hoffner, Deephaven, MN (US); Kelsey Isenberg, Morristown, NJ (US); Melissa Jeanne Umenhofer, Manchester, NH (US); Damian Kelly, Kilcock (IE); Anthony A. Nguyen, Pacific Palisades, CA (US)

(73) Assignee: UNITEDHEALTH GROUP INCORPORATED, Minnetonka, MN (US)

( * ) Notice: Subject to any disclaimer, the term of this patent is extended or adjusted under 35 U.S.C. 154(b) by 534 days.

(21) Appl. No.: 17/248,724

(22) Filed: Feb. 4, 2021

(65) Prior Publication Data

US 2022/0246286 A1 Aug. 4, 2022

(51) Int. Cl.
*G06Q 10/10* (2023.01)
*G06F 16/27* (2019.01)
(Continued)

(52) U.S. Cl.
CPC ............. *G16H 40/20* (2018.01); *G06F 16/27* (2019.01); *G06N 3/044* (2023.01); *G06N 3/045* (2023.01);
(Continued)

(58) Field of Classification Search
CPC ........ G16H 40/20; G16H 10/60; G16H 50/20; G06N 3/044; G06N 3/045; G06N 3/08;
(Continued)

(56) References Cited

U.S. PATENT DOCUMENTS

| 8,784,311 B2 | 7/2014 | Shrivastav et al. |
| 10,650,844 B2 | 5/2020 | Meshram et al. |

(Continued)

FOREIGN PATENT DOCUMENTS

WO 2019060878 A1 3/2019

OTHER PUBLICATIONS

Basu et al., "Emotion recognition from speech using convolutional neural network with recurrent neural network architecture," 2017 2nd International Conference on Communication and Electronics Systems (ICCES), Coimbatore, India, 2017, pp. 333-336 (Year: 2017).*

(Continued)

*Primary Examiner* — Jonathan Ng
*Assistant Examiner* — Benjamin L. Hanks
(74) *Attorney, Agent, or Firm* — Shumaker & Sieffert, P.A.

(57) ABSTRACT

An example method includes obtaining, by a computing system, audio data representing sounds generated by a user; applying, by the computing system, a machine learning (ML) model that generates output data based on non-semantic content of the audio data; and generating, by the computing system, based on the output data generated by the ML model, a recommended healthcare provider list for the user, the recommended healthcare provider list for the user including one or more healthcare providers recommended for the user.

16 Claims, 4 Drawing Sheets

(51) Int. Cl.
*G06N 3/044* (2023.01)
*G06N 3/045* (2023.01)
*G06N 3/08* (2023.01)
*G06Q 40/08* (2012.01)
*G10L 15/183* (2013.01)
*G16H 10/60* (2018.01)
*G16H 40/20* (2018.01)
*G16H 50/20* (2018.01)
*G06F 17/14* (2006.01)

(52) U.S. Cl.
CPC .............. *G06N 3/08* (2013.01); *G06Q 10/10* (2013.01); *G06Q 40/08* (2013.01); *G10L 15/183* (2013.01); *G16H 10/60* (2018.01); *G16H 50/20* (2018.01); *G06F 17/142* (2013.01)

(58) Field of Classification Search
CPC ...... G06Q 10/10; G06Q 40/08; G10L 15/183; G06F 17/142
See application file for complete search history.

(56) References Cited

U.S. PATENT DOCUMENTS

| | | | |
|---|---|---|---|
| 2016/0371439 A1 | 12/2016 | Salazar et al. | |
| 2019/0237203 A1* | 8/2019 | Schwabl | G06Q 10/1095 |
| 2019/0385711 A1* | 12/2019 | Shriberg | G16H 10/20 |
| 2019/0385753 A1 | 12/2019 | Aganyan et al. | |
| 2020/0020335 A1 | 1/2020 | Liu | |
| 2020/0137230 A1 | 4/2020 | Spohrer | |
| 2021/0334697 A1* | 10/2021 | Hanley | G06N 3/08 |

OTHER PUBLICATIONS

Kruzan, "VOCAL Algorithms Identify the Best Providers Based on User Preference," Perception Health, Retrieved Jun. 22, 2021, from: https://www.perceptionhealth.com/research/vocal-physician-matching-algorithm, Mar. 28, 2019, 6 pp.

* cited by examiner

USE OF AUDIO DATA FOR MATCHING PATIENTS WITH HEALTHCARE PROVIDERS

BACKGROUND

Patients are frequently able to choose their own healthcare providers from among the healthcare providers available in their areas. For example, a patient might be able to choose among a set of primary care physicians that are within the network of the patient's health insurance provider. Choosing a healthcare provider can be a difficult challenge for a patient, especially when the patient is not certain what type of healthcare provider is best suited for the patient's needs.

SUMMARY

The present disclosure describes devices, systems, and methods for automatically matching patients with healthcare providers. As described herein, a computing system obtains audio data representing sounds generated by a user, such as a patient. In some examples, the audio data may be generated as part of an interaction between the user and an interactive voice assistant, such as ALEXA from Amazon.com Inc. or SIRI from Apple Inc. The computing system applies a machine learning (ML) model that generates output data based on non-semantic content of the audio data, such as vocal biomarkers. Based on this output data, the computing system may generate a recommended healthcare provider list for the user. The recommended healthcare provider list for the user includes one or more healthcare providers recommended for the user.

In one example, this disclosure describes a method includes obtaining, by a computing system, audio data representing sounds generated by a user; applying, by the computing system, a machine learning (IL) model that generates output data based on non-semantic content of the audio data; and generating, by the computing system, based on the output data generated by the ML model, a recommended healthcare provider list for the user, the recommended healthcare provider list for the user including one or more healthcare providers recommended for the user.

In another example, this disclosure describes a computing system includes processing circuitry configured to: apply a machine learning (ML) model that generates output data based on non-semantic content of audio data representing sounds generated by a user; and generate, based on the output data generated by the ML model, a recommended healthcare provider list for the user, the recommended healthcare provider list for the user including one or more healthcare providers recommended for the user; and a communication unit configured to send the recommended healthcare provider list.

In another example, this disclosure describes a computer-readable storage medium comprising instructions that, when executed, cause one or more processors to: obtain audio data representing sounds generated by a user; apply a machine learning (ML) model that generates output data based on non-semantic content of the audio data; and generate, based on the output data generated by the ML model, a recommended healthcare provider list for the user, the recommended healthcare provider list for the user including one or more healthcare providers recommended for the user.

The details of one or more aspects of the disclosure are set forth in the accompanying drawings and the description below. Other features, objects, and advantages of the techniques described in this disclosure will be apparent from the description, drawings, and claims.

DETAILED DESCRIPTION

Choosing a healthcare provider for a user can be challenging. For instance, there might be many healthcare providers that are available to a user, but it may be difficult for the user to know which of the available healthcare providers is best suited for the user's needs. There are several problems associated with developing an automated system that generates personalized recommendations of healthcare providers. For instance, the user may not be consciously aware of specific types of symptoms that could guide a healthcare provider recommendation process. Moreover, some such symptoms may not even be detectible to other human users, such as an appointments clerk or triage nurse. For example, certain non-semantic content of audio data, such as vocal biomarkers in the user's voice, can indicate the presence or absence of specific conditions that may be useful in guiding a healthcare provider recommendation process. Additionally, there may be many factors that go into why users choose specific healthcare providers. It may be time consuming and burdensome for the user to input data indicating such factors into a recommendation system. For instance, the user may need to fill out an extensive form or answer numerous questions to provide information that the recommendation system could use to determine recommended healthcare providers for the user.

This disclosure describes techniques that may address one or more of these issues. As described herein, a computing system may obtain audio data representing sounds generated by a user. The computing system may apply a ML model that generates output data based on a set of inputs, which may include non-semantic data of the audio data. Furthermore, the computing system may generate, based on the output data generated by the ML model, a recommended healthcare provider list for the user. The recommended healthcare provider list for the user includes one or more healthcare providers recommended for the user. Because the input of the ML model includes the non-semantic content, the recommended healthcare provider list for the user may be better suited to the user's needs.

Figure 1:
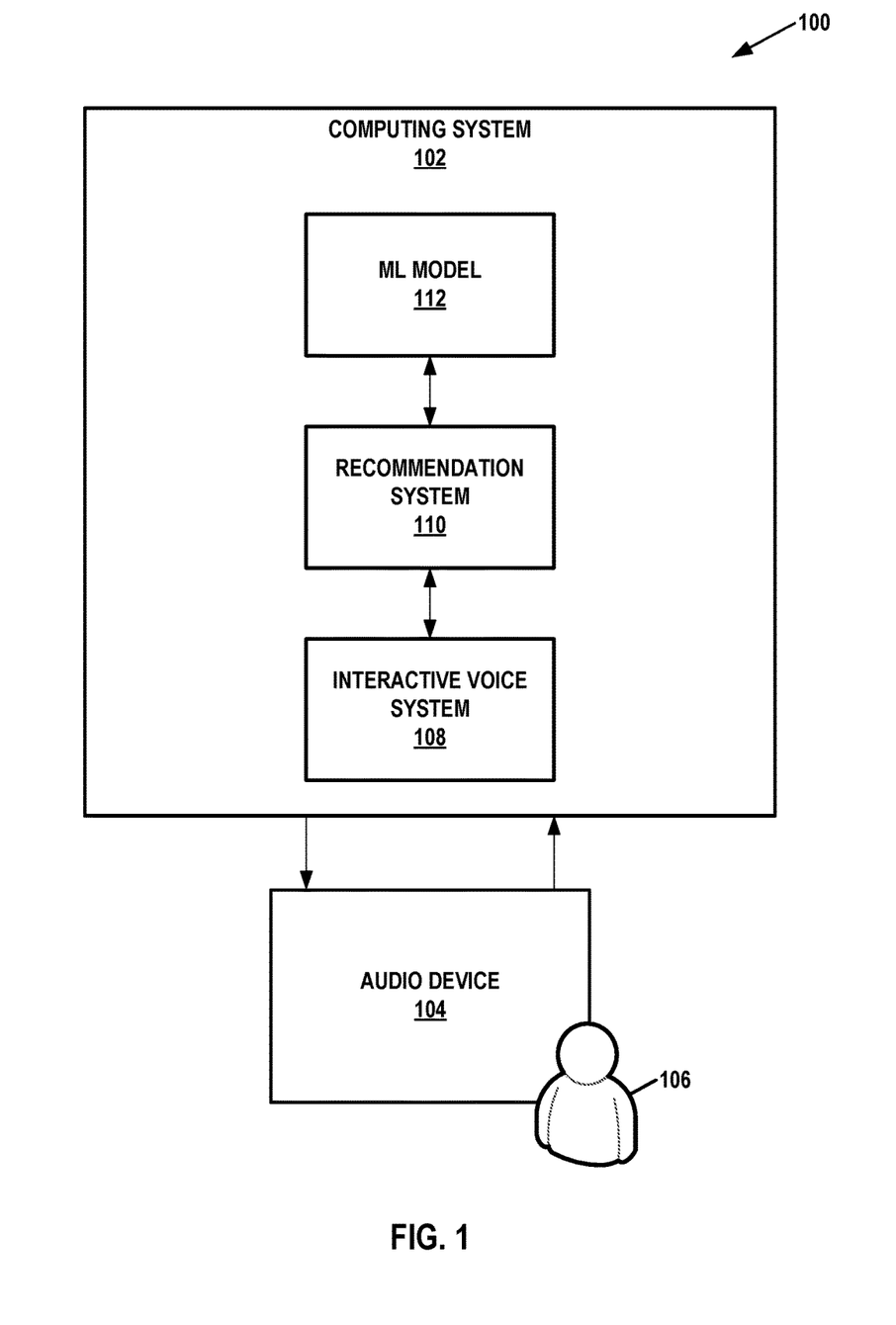
FIG. 1 is a block diagram illustrating an example system in accordance with one or more aspects of this disclosure.

FIG. 1 is a block diagram illustrating an example system 100 in accordance with one or more aspects of this disclosure. In the example of FIG. 1, system 100 includes a computing system 102 and an audio device 104. In other examples, system 100 may include more, fewer, or different components.

Computing system 102 may include one or more computing devices. In examples where computing system 102 includes two or more computing devices, the computing devices of computing system 102 may act together as a system. Example types of computing devices include server devices, personal computers, handheld computers, intermediate network devices, data storage devices, and so on. In examples where computing system 102 includes two or more computing devices, the computing devices of computing system 102 may be geographically distributed or concentrated together (e.g., in a single data center).

Audio device 104 is configured to generate audio data representing sounds generated by a user 106. Audio device 104 may also be configured to generate sound based on audio data generated by computing system 102 or another source. Audio device 104 may also include one or more devices. For example, audio device 104 may include a smart speaker device, a personal computer, a mobile phone, a tablet computer, an ambient computing device, an Internet of Things (IoT) device, or another type of device. Computing system 102 and audio device 104 may be configured to communicate via one or more communication networks, such as the Internet. In some examples, audio device 104 is included in the one or more computing devices of computing system 102.

In the example of FIG. 1, computing system 102 is configured to implement an interactive voice system 108, a recommendation system 110, and a machine learning (ML) model 112. Interactive voice system (IVS) 108 may be configured to obtain audio data from audio device 104 and process the audio data to determine semantic content of the audio data. In other words, IVS 108 may determine what speech sounds represented by the audio data mean. Additionally, IVS 108 may send response audio data to audio device 104. The response audio data may represent sound that may, e.g., be responsive to the semantic content of the audio data obtained from audio device 104. In some examples, IVS 108 may be or may include a voice assistant system, such as ALEXA by Amazon.com Inc., SIRI by Apple Inc., CORTANA by Microsoft Corp., or another type of voice assistant system. In some examples, IVS 108 may include a voice user interface system. Although depicted in the example of FIG. 1 as being part of computing system 102, some or all of the functionality of IVS 108 may be implemented in audio device 104 or another device. For instance, some of the functionality of IVS 108 may be implemented in audio device 104 and some of the functionality of IVS 108 may be implemented in computing system 102.

User 106 may engage in an interactive voice session with IVS 108. During an interactive voice session with IVS 108, user 106 may utter various types of statements to audio device 104. Example types of statements may include requests, responses to questions, formalities, commands, and so on. For example, user 106 may utter a spoken request to audio device 104 to request a visit to a healthcare provider. In another example, user 106 may utter a spoken request to audio device 104 to request a list of suitable healthcare providers. In some examples, user 106 may utter a spoken request to schedule or confirm an appointment with a healthcare provider. Audio device 104 may send audio data representing the utterances to IVS 108.

Audio device 104 may obtain response audio data from IVS 108, e.g., in response to the audio data sent by audio device 104, and output sound based on the response audio data. For instance, user 106 may say "I'd like to schedule an appointment with a dermatologist" and audio device 104 may say "I can help you with that" based on response audio data generated by IVS 108. In some examples where audio device 104 includes a display screen, audio device 104 may receive data from computing system 102 representing a healthcare provider list and may display the healthcare provider list on the display screen.

In some examples, IVS 108 provides semantic data to recommendation system 110. For example, if the audio data obtained by IVS 108 represents speech indicating a request to visit a physical therapist, IVS 108 may provide semantic data to recommendation system 110 indicating that user 106 wants to visit a physical therapist. Furthermore, in accordance with one or more techniques of this disclosure, IVS 108 may provide some or all of the audio data to recommendation system 110. In some examples, recommendation system 110 may be a "skill" of a voice assistant system.

Based on the semantic data indicating that user 106 wishes to receive a recommendation of one or more healthcare providers, recommendation system 110 may use ML model 112 to generate output data. Recommendation system 110 may generate a recommended healthcare provider list for user 106 based on the output data generated by ML model 112. The recommended healthcare provider list for user 106 may include one or more healthcare providers recommended for user 106. Input to ML model 112 may include one or more aspects of the semantic data, the audio data, and other types of data.

When applying ML model 112, recommendation system 110 may extract non-semantic content of the audio data and may generate the output data based at least in part on the non-semantic content of the audio data. The non-semantic content includes information conveyed by sounds generated by the user other than the meanings of words expressed in the sounds. For example, recommendation system 110 may extract vocal biomarkers of user 106 from the audio data. A vocal biomarker of user 106 is an aspect of the sounds the voice of user 106 separate from semantic meaning of the sounds. Other types of non-semantic content may include the sound of coughing, wheezing, or other types of non-vocal sounds made by user 106. The extracted non-semantic content may be indicative of specific types of health conditions that may be relevant in recommending healthcare providers to user 106. For example, the extracted non-semantic content (e.g., in conjunction with data generated by applying emotional sentiment analysis to the audio data) may indicate that user 106 is experiencing or at risk of experiencing depression, even if user 106 does not explicitly report experiencing depression. In some examples, the extracted non-semantic content may indicate that user 106 has a condition such as Parkinson's disease (which may present in the form of vocal tremors in the voice of user 106), depression and/or mania (which may present in the form of tone and affect of the speech of user 106), coronary artery disease and/or pulmonary hypertension (which may present in the form of intensity and frequency changes in the voice of user 106), schizophrenia (which may present in the form of affect changes, pitch variability, rate changes, changes in pause frequency, and so on, in the voice of user 106), nasal congestion, emphysema, pharyngitis, tonsillitis, and other types of conditions. In some examples, the extracted non-semantic content indicate whether user 106 has a cough and may indicate specific characteristics of the cough. Generating the output data based on the non-semantic content may help recommendation system 110 generate a recommended healthcare provider list that is potentially better suited to the needs of user 106.

In some examples, after recommendation system 110 generates the recommended healthcare provider list for user 106, IVS 108 may generate audio data representing the recommended healthcare provider list for user 106. Audio device 104 may generate sound based on the audio data generated by IVS 108. In this way, user 106 may be able to hear the recommended healthcare provider list. In other examples, devices other than audio device 104 may receive the audio data from computing system 102 and generate sound based on the audio data.

In some examples audio device 104 includes a display screen and computing system 102 may generate data that computing system 102 sends to audio device 104. Audio device 104 may display the recommended healthcare provider list on the display screen. For example, computing system 102 may generate Hypertext Markup Language (HTML) data, comma separated value (CSV) data, or another type of data that audio device 104 may use to display the recommended healthcare provider list on the display screen. In other examples, devices other than audio device 104 may receive data from computing system 102 and display the recommended healthcare provider list. In other examples, computing system 102 may send a message, such as an email message or text message, containing the recommended healthcare provider list.

Figure 2:
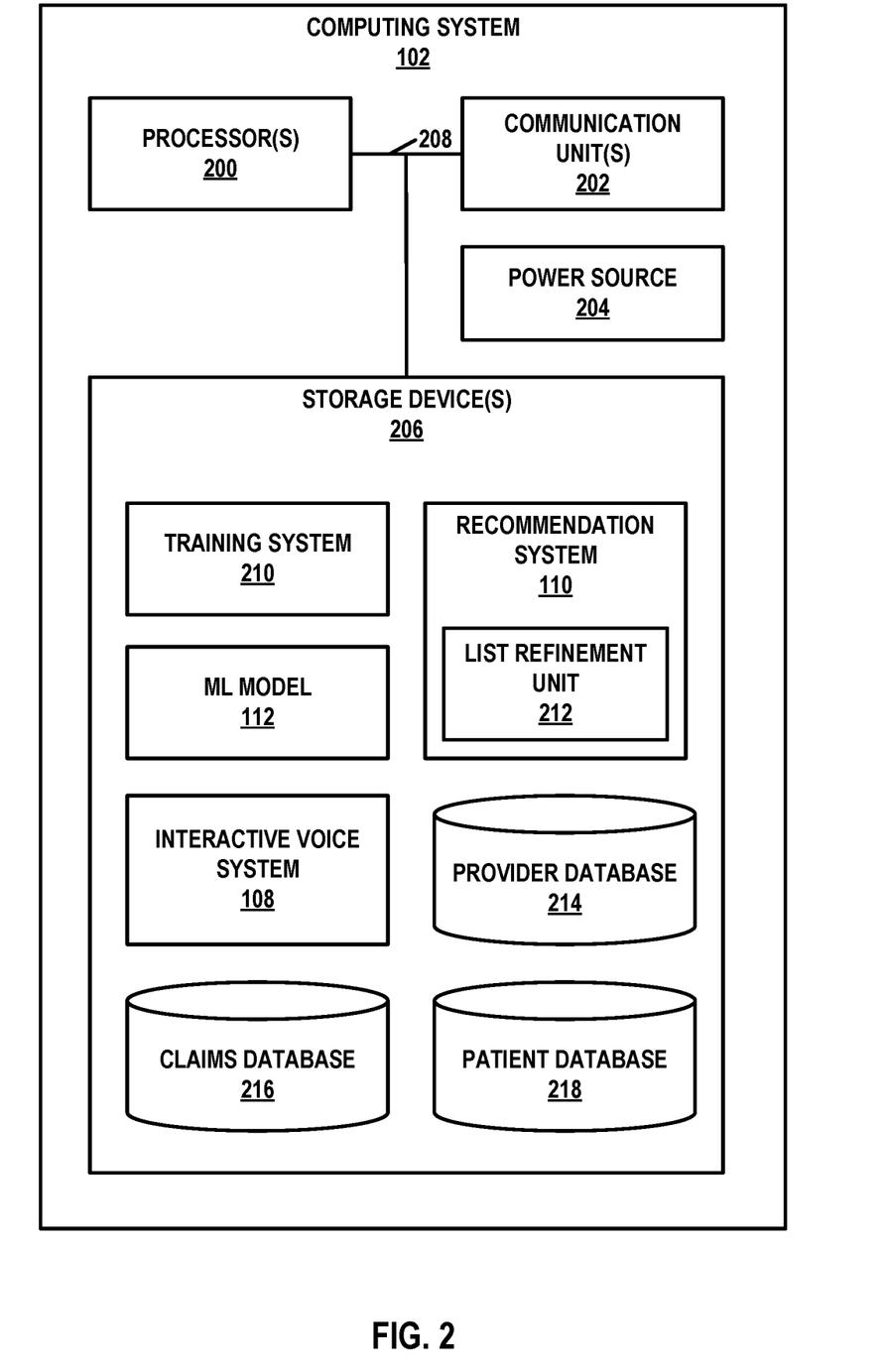
FIG. 2 is a block diagram illustrating example components of a computing system in accordance with one or more aspects of this disclosure.

FIG. 2 is a block diagram illustrating example components of computing system 102 in accordance with one or more aspects of this disclosure. FIG. 2 illustrates only one example of computing system 102, without limitation on many other example configurations of computing system 102.

As shown in the example of FIG. 2, computing system 102 includes one or more processors 200, one or more communication units 202, a power source 204, one or more storage devices 206, and one or more communication channels 224. Computing system 102 may include other components. For example, computing system 102 may include input devices, output devices, display screens, and so on. Communication channel(s) 224 may interconnect each of components 200, 202, and 206 for inter-component communications (physically, communicatively, and/or operatively). In some examples, communication channel(s) 224 may include a system bus, a network connection, an inter-process communication data structure, or any other method for communicating data. Power source 204 may provide electrical energy to components 200, 202, and 206. Storage device(s) 206 may store information required for use during operation of computing system 102.

Processor(s) 200 comprise circuitry configured to perform processing functions. For instance, one or more of processor(s) 200 may be a microprocessor, application-specific integrated circuit (ASIC), field-programmable gate array (FPGA), or other type of processing circuit. In some examples, processor(s) 200 of computing system 102 read and may execute instructions stored by storage device(s) 206. Processor(s) 200 may include fixed-function processors and/or programmable processors.

Communication unit(s) 202 may enable computing system 102 to send data to and receive data from one or more other computing devices (e.g., via a communications network, such as a local area network or the Internet). For instance, communication unit(s) 202 may be configured to send notifications to subscribers, receive subscriber responses, send notifications to organizations, and so on. In some examples, communication unit(s) 202 may include wireless transmitters and receivers that enable computing system 102 to communicate wirelessly with other computing devices. Examples of communication unit(s) 202 may include network interface cards, Ethernet cards, optical transceivers, radio frequency transceivers, or other types of devices that are able to send and receive information. Other examples of such communication units may include BLU-ETOOTH™, 3G, 4G, 5G, and WI-FI™ radios, Universal Serial Bus (USB) interfaces, etc. Computing system 102 may use communication unit(s) 202 to communicate with one or more other computing devices or systems, such as audio device 104.

Processor(s) 200 may read instructions from storage device(s) 206 and may execute instructions stored by storage device(s) 206. Execution of the instructions by processor(s) 200 may configure or cause computing system 102 to provide at least some of the functionality ascribed in this disclosure to computing system 102.

As shown in the example of FIG. 2, storage device(s) 206 include computer-readable instructions associated with IVS 108, recommendation system 110, and a training system 210. Furthermore, in the example of FIG. 2, the computer-readable instructions associated with recommendation system 110 may include computer-readable instructions associated with a list refinement unit 212.

Additionally, in the example of FIG. 2, storage devices(s) 206 may include a provider database 214, a claims database 216, and a patient database 218. Provider database 214 may store information about healthcare providers. For example, provider database 214 may store user reviews of providers, years of experience, types of experience of the healthcare provider, research and academic contributions, clinical trial participation, academic publications, Centers for Medicare & Medicaid Services (CMS) grant funding, impact factor (publications) of the healthcare provider, conditions managed by the healthcare provider, and so on. Such data may be used as input to ML model 112 or as a basis for forming input to ML model 112.

Claims database 216 may store claims data that contains information about health insurance claims filed by users, such as user 106. The claims data may indicate which healthcare provider provided healthcare services, the type of healthcare services provided, type of conditions treated, and so on. Patient database 218 may store other types of data regarding patients. Such data may be used as input to ML model 112 or as a basis for forming input to ML model 112.

In the example of FIG. 2, IVS 108 may obtain audio data representing sounds generated by user 106. IVS 108 may process the audio data to extract semantic content from the audio data. For example, IVS 108 may convert the audio data to text and interpret the text to determine an intent of user 106. Based on the semantic content of the audio data, IVS 108 may determine that the intent of user 106 is to obtain a recommended healthcare provider list.

Based on IVS 108 determining that the intent of user 106 is to obtain a recommended healthcare provider list, IVS 108 may provide the audio data to recommendation system 110. In other examples, recommendation system 110 may obtain the audio data in other ways.

The audio data obtained by recommendation system 110 may comprise a series of samples grouped into frames. Recommendation system 110 may perform a data preparation process on the audio data. The data preparation process may prepare the audio data for use as input by ML model 112. For instance, in some examples, as part of performing the data preparation process, recommendation system 110 may apply a Fast Fourier Transform (FFT) to the audio data. By applying the FFT to a frame of the audio data, recommendation system 110 may generate an array (e.g., 1-dimensional (1D) array, 2-dimensional (2D) array, etc.) of transform coefficients in a frequency domain. In this example, recommendation system 110 may provide the array of transform coefficients to ML model 112 as input. In other examples, IVS 108 or another system may perform the data preparation process. For instance, IVS 108 may apply the FFT to the audio data to generate the array of transform coefficients.

Recommendation system 110 may also provide supplemental data as input to ML model 112. In some examples, the supplemental data is organized into tables. Hence, the supplemental data may be referred to as tabular data. The supplemental data may include data from provider database 214, claims database 216, patient database 218, and/or other sources of data.

Recommendation system 110 may apply ML model 112 to generate output data based on input data, such as the audio data (e.g., in the form of an array of transform coefficients, spectrogram, etc.) and the supplemental data. An example architecture of ML model 112 is described with respect to FIG. 3. As part of applying the ML model 112, recommendation system 110 may extract one or more types of non-semantic content, such as vocal biomarkers, from the audio data. Example types of vocal biomarkers may include spectral features (e.g., Mel-frequency cepstral coefficients, perceptual linear prediction, etc.), prosodic features (e.g., speaking rate, pitch, intensity, etc.), voice quality features (e.g., shimmer, jitter local, an absolute difference of differences between jitter cycles, harmonics-to-noise ratio, etc.), language features (e.g., 1-gram word probability, pause filler ratio, etc.), and so on.

List refinement unit 212 of recommendation system 110 may generate the recommended healthcare provider list based on the output data generated by ML model 112. For example, the output data may specify a score for each healthcare provider in a set of healthcare providers. In some examples, the score for a healthcare provider is a probability of the healthcare provider being a good match for user 106. In such examples, the output data may be referred to as a provider match probability vector.

As part of generating recommended healthcare provider list, list refinement unit 212 may order the healthcare providers based on the scores for the healthcare providers. For instance, list refinement unit 212 may rank the healthcare providers from high-to-low scores, or vice versa. In some examples, list refinement unit 212 may arrange the healthcare providers in an order different from an order based strictly on the scores for the healthcare providers as indicated by the output data generated by ML model 112. For instance, list refinement unit 212 may determine weighted scores for the healthcare providers that use the scores generated by ML model 112 as one component. Other components may include one or more of healthcare provider years of experience, healthcare provider rating, distance from user 106, compliance with preferences of user 106, and so on.

Furthermore, list refinement unit 212 may filter the healthcare providers in the recommended healthcare provider list. For example, list refinement unit 212 may apply a filter that eliminates healthcare providers that are located more than a specific distance from a location of user 106. In some examples, list refinement unit 212 may apply a filter that eliminates healthcare providers that are within or outside of specific postal codes (e.g., zip codes). In some examples, list refinement unit 212 may apply a filter that eliminates healthcare providers that do not provide a specialty (e.g., cardiology, oncology, gynecology, etc.) needed or desired by user 106.

In some examples, list refinement unit 212 may apply a filter that eliminates healthcare providers that do not satisfy the preferences of user 106. Data indicating the preferences of user 106 may be stored in patient database 218. Example preferences may include minimum years of experience, whether transportation to the healthcare provider is available, minimum healthcare provider rating, aggregate patient review rating of the healthcare provider, gender of the healthcare provider, age of healthcare provider, languages spoken by the healthcare provider, whether the healthcare provider is child-friendly, location of the healthcare provider, location type of healthcare provider (e.g., rural, urban, etc.), whether other family members have visited the healthcare provider, when the healthcare provider has available appointments, whether the healthcare providers have patient portal capabilities, and so on. In some examples where list refinement unit 212 filters the healthcare providers based on geographic location and based on whether transportation is available, list refinement unit 212 may limit the healthcare providers to those that are within range of the available transportation (which may be defined in a health insurance policy of user 106, provider database 214, or another data source).

In some examples, recommendation system 110 may infer one or more types of preference of user 106 rather than having user 106 explicitly indicate their preferences. For instance, recommendation system 100 may be able to infer based on claims data for user 106 that user 106 prefers healthcare providers that are in larger cities than healthcare providers in the countryside, infer that user 106 prefers appointments in the evening, infer that user 106 prefers healthcare providers visited by family members, and so on.

In some examples, list refinement unit 212 may supplement the recommended healthcare provider list with information about the healthcare providers. For example, list refinement unit 212 may supplement recommended healthcare provider list about the healthcare providers from provider database 214. Such information may include addresses of the healthcare providers, patient ratings of the healthcare providers, links to websites of the healthcare providers, information regarding prices charged by the healthcare providers, and so on.

As noted elsewhere in this disclosure, list refinement unit 212 may filter or order the healthcare providers based on provider ratings for the healthcare providers. For instance, in one example, list refinement unit 212 may filter out healthcare providers that are outside a postal code of user 106 and then sort by provider ratings for the remaining healthcare providers. In this example, list refinement unit 212 may generate the recommended healthcare provider list such that the recommended healthcare provider list includes only the top-rated remaining healthcare provider, or a set of two or more of the top-rated remaining healthcare providers. In some examples where list refinement unit 212 filters the healthcare providers based on provider ratings and there are no healthcare providers that have a minimum provider rating specified by user 106 within a geographic area associated with user 106, list refinement unit 212 may include, in the recommended healthcare provider list, a top-rated healthcare provider outside the geographic area and also include one or more healthcare providers that are within the geographic area but that do not satisfy the minimum provider rating.

In some examples, list refinement unit 212 may filter the healthcare providers based on health conditions of user 106. For example, recommendation system 110 (e.g., list refinement unit 212) may determine scan claims database 216, patient database 218, and/or other data sources to determine health conditions of user 106. Recommendation system 110 may filter and/or sort the health conditions of user 106 based on recency to determine the health conditions that are most likely to be relevant to user 106. In some examples, list refinement unit 212 may identify the health conditions of user 106 based on symptoms reported by user 106, e.g., in patient database, during a voice interaction session with IVS 108, symptoms noted in healthcare provider generated notes for user 106, or elsewhere. In examples where list refinement unit 212 filters the healthcare providers based on health conditions of user 106, list refinement unit 212 may determine (e.g., based on data in provider database) which of the healthcare providers are within a geographic area associated with user 106 and also provide treatment for the health conditions of user 106.

In some examples, list refinement unit 212 may choose different geographical filters for filtering healthcare providers based on a disease severity of user 106 and/or whether the condition of user 106 is chronic or acute. For example, list refinement unit 212 may use a broad geographic filter (e.g., 100 miles) when user 106 has cancer versus a narrow geographic filter (e.g., 5 miles) when user 106 is seeking an eye examination for corrective eyewear.

In some examples, list refinement unit 212 may reorder the recommended healthcare provider list based on availability of the healthcare providers in the recommended healthcare provider list. For example, list refinement unit 212 may access scheduling systems associated with the healthcare providers to determine available appointment times. In this example, list refinement unit 212 may reorder the recommended healthcare provider list to prioritize healthcare providers with earlier available appointments. For example, a head and neck surgeon available tomorrow may have a higher weighted score than a head and neck surgeon with equal scoring but not available for another 3 months.

In some examples, list refinement unit 212 may reorder the recommended healthcare provider list based on typical wait times for the healthcare providers. For example, list refinement unit 212 may reorder the recommended healthcare provider list based on average wait-time for a given hospital or practice in order to further differentiate the healthcare providers due to availability. For example, if two OBGYNs are available next week, but one OBGYN has an office wait-time of 2 hours they would receive a lower weighted score than the other OBGYN with an average wait-time of 15 minutes. In some examples, the typical wait times for healthcare providers may be part of the supplemental data provided as input to ML model 112.

Recommendation system 110 may provide the recommended healthcare provider list to IVS 108. IVS 108 may then generate audio data based on the recommended healthcare provider list. IVS 108 may then provide the audio data to audio device 104. In some examples, computing system 102 may provide other types of data representing the recommended healthcare provider list that a device may use to display the recommended healthcare provider list.

In some examples, recommendation system 110 receives healthcare provider selection input that indicates a selected healthcare provider from the recommended healthcare provider list. For example, IVS 108 may receive audio data representing the sound of user 106 indicating the selected healthcare provider (e.g., "I'd like make an appointment at Main Street Family Medicine"). In this example, IVS 108 may provide the audio data or data representing semantic content of the audio data to recommendation system 110.

Based on the healthcare provider selection input, recommendation system 110 may perform one or more tasks to help user 106 schedule an appointment with the selected healthcare provider. For example, recommendation system 110 may send a message to a computer system associated with the selected healthcare provider. The computing system associated with the selected healthcare provider may automatically prompt a worker to contact user 106, e.g., by text, telephone, or email. In some examples, recommendation system 110 may interact with a computer system associated with the selected healthcare provider to determine available appointment times. In this example, recommendation system 110 may provide data indicating the available appointment times to IVS 108, which may generate audio data indicating the available appointment times. Furthermore, in this example, IVS 108 may receive audio data indicating a selected appointment time (e.g., "I'd like the appointment time at 9:30 on Tuesday."). In this example, recommendation system 110 may interact with the computing system associated with the selected healthcare provider to schedule an appointment for user 106 at the selected appointment time.

In some examples, recommendation system 110 may provide additional information about user 106 (e.g., with the permission of user 106) to the selected healthcare provider. The provided information may help the selected healthcare provider provide healthcare to user 106. For example, recommendation system 110 may determine based on the non-semantic content (e.g., vocal biomarkers) that user 106 may have a specific condition, such as depression. In some examples, recommendation system 110 may determine whether user 106 has the specific condition as part of applying ML model 112 or another ML model. In this example, the information provided to the selected healthcare provider may indicate that user 106 is at risk of depression. In another example, recommendation system 110 may determine that user 106 may have a specific health condition (e.g., Parkinson's disease, schizophrenia, coronary artery disease, hypertension, coughing, etc.) based on the non-semantic content. In this example, recommendation system 110 may provide an indication of this specific health condition to the selected healthcare provider.

In some examples, the non-semantic content may include indications that user 106 has a cough. Recommendation system 110 may provide information about the cough to the selected healthcare provider. Furthermore, in some examples, recommendation system 110 may analyze the cough to determine whether the cough is consistent with a particular type of infectious disease, such as tuberculosis. Such analysis may be performed by ML model 112, another ML model, or a separate system. In such examples, the selected healthcare provider may make a determination about whether or how to schedule an appointment with the patient based on whether user 106 has the particular type of disease. For instance, if user 106 has a cough that is consistent with a particular type of infectious disease, the selected healthcare provider may schedule a telemedicine visit instead of an in-person visit or may request user 106 take a test for the infectious disease before an in-person visit.

In the example of FIG. 2, training system 210 is configured to train ML model 112. In some examples, training system 210 may obtain a training data set that includes training data pairs. Each of the training data pairs includes an input dataset and a target. The input dataset of a training data pair may include data based on audio data and may include supplemental data. The output dataset of a training data pair indicates a healthcare provider. Training system 210 may provide the input dataset of a training data pair as input to ML model 112. Training system 210 may then calculate an error value based on a difference between the output of ML model 112 and the target of the training data pair. Additionally, training system 210 may perform a backpropagation algorithm using the error value to update parameters (e.g., weights of artificial neurons of the one or more neural networks) of ML model 112.

As mentioned elsewhere in this disclosure, recommendation system 110 may receive healthcare provider selection input. In some examples, training system 210 may use the healthcare provider selection input as a basis for training ML model 112. For instance, in one example, training system 210 may generate a training data pair that includes an input dataset and a target. In this example, the input dataset may include all of input data, e.g., including voice data and supplemental data. Furthermore, in this example, the target may specify a healthcare provider specified by the healthcare provider selection input. In this example, training system 210 may use the generated training data pair to continue training ML model 112, e.g., in the manner described elsewhere in this disclosure.

In some examples where the recommended healthcare provider list is presented on a touch-sensitive display screen, user 106 may provide the healthcare provider selection input in the form of swiping left (or swiping right) to reject a healthcare provider in the recommended healthcare provider list or swiping right (or swiping left) to accept a healthcare provider in the recommended healthcare provider list.

In some examples, training system 210 may generate training data pairs based on data in claims database 216. For example, even if recommendation system 110 does not receive a healthcare provider selection input, claims database 216 may include claims data that indicate a healthcare provider from whom user 106 eventually sought care. Training system 210 may match the input data for user 106 (including e.g., data based on voice data and supplemental data) with an indication of the healthcare provider from whom user 106 sought care to generate a training data pair. Training system 210 may then use the training data pair to continue training ML model 112. For instance, in one example, the following table may show the output data generated by ML model 112 for a given input dataset:

|  | Prediction |
|---|---|
| Provider A | 0.8 |
| Provider B | 0.1 |
| Provider C | 0.1 |

In this example, if user 106 selects Provider B, training system 210 may generate following the target data:

|  | Label |
|---|---|
| Provider A | 0 |
| Provider B | 1 |
| Provider C | 0 |

Training system 210 may use the generated target data and the given input dataset as a training data pair for training ML model 112. Thus, in some examples, training system 210 of computing system 102 may generate training data based on health insurance claims data that indicate a healthcare provider from the recommended healthcare provider list that was visited by user 106 and may train the ML model based on the training data.

Components of computing system 102 may be contained within a single device or distributed among multiple devices. For example, IVS 108 is implemented by devices remote from devices that implement recommendation system 110. For instance, IVS 108 may be implemented on a set of servers that provide a voice assistant system and recommendation system 110 may be implemented on a separate set of servers. In some examples, communication unit(s) 202 may send the recommended healthcare provider list, e.g., to IVS 108, audio device 104, or another device.

Figure 3:
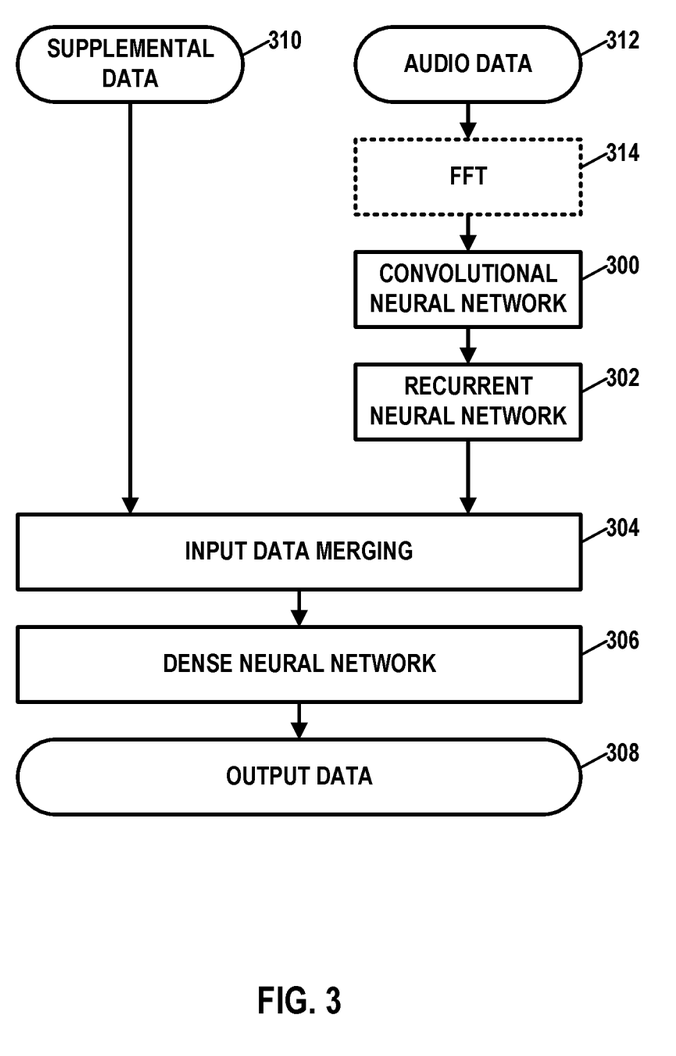
FIG. 3 is a block diagram illustrating an example architecture of a machine learning model in accordance with one or more techniques of this disclosure.

FIG. 3 is a block diagram illustrating an example architecture of ML model 112 in accordance with one or more techniques of this disclosure. In the example of FIG. 3, ML model 112 is a deep learning model. Recommendation system 110 may apply ML model 112 to generate output data that may be used in generate a recommended healthcare provider list. Thus, in some examples, recommendation system 110 may be able to predict a most appropriate healthcare provider for user 106.

In the example of FIG. 3, ML model 112 includes a convolutional neural network (CNN) 300, a recurrent neural network (RNN) 302, an input data merging layer 304, and a dense neural network 306. ML model 112 may generate output data 308 based on audio data 312 and supplemental data 310. In the example of FIG. 3, recommendation system 110 may apply an FFT 314 to frames of audio data 312 to generate arrays of transform coefficients that recommendation system 110 may provide as input to CNN 300. In some examples, a memory, such as storage device(s) 206 (FIG. 2) may store audio data 312.

In some examples, CNN 300 is implemented as a 1-dimensional convolutional neural network. In such examples, input to CNN 300 (e.g., an array of transform coefficients) may be in the form of a 1-dimensional array. In some examples, RNN 302 may be implemented using one or more Gated Recurrent Units (GRUs). In some examples, RNN 302 may be implemented using a Long Short-Term Memory (LSTM). Together CNN 300 and RNN 302 may extract non-semantic content from audio data 312. More specifically, CNN 300 may be configured to extract non-semantic content that may be detected within a single frame of audio data 312. RNN 302 may be configured to extract non-semantic content from across multiple frames of audio data 312. Thus, in the example of FIG. 3, recommendation system 110 may apply a FFT to audio data 312 to determine an array of transform coefficients and, as part of extracting the one or more non-semantic content, recommendation system 110 may apply CNN 300 to the array of transform coefficients to generate first intermediate output. Furthermore, recommendation system 110 may apply a second ML model (e.g., RNN 302) to the first intermediate output to extract the non-semantic content.

Input data merging layer 304 may merge the data generated by RNN 302 with supplemental data 310 to form input data for dense neural network 306. Supplemental data 310 may include a variety of data, including data that is not based on audio data 312.

In some examples, supplemental data 310 includes data from patient database 218. The data from patient database 218 may include demographic data for user 106. Example types of demographic data (e.g., age of user 106, gender of user 106, etc.), data regarding a health insurance policy of user 106 (e.g., an indication of an in-network provider network associated with a health insurance policy of user 106, an indication of healthcare services covered by the health insurance policy of user 106, etc.), data regarding a location of user 106, and so on.

In some examples, supplemental data 310 includes data regarding health conditions of user 106. For instance, in some examples, IVS 108 may receive audio data representing symptoms or health conditions reported by user 106. In such examples, IVS 108 may provide data (e.g., tabular data, audio data, etc.) regarding such symptoms or health conditions to recommendation system 110, which may process the data for including in supplemental data 310.

In some examples, recommendation system 110 may obtain the data regarding the health conditions of user 106 from patient database 218, claims database 216, or another data source. For instance, recommendation system 110 may obtain data regarding the health conditions (e.g., the top x number of health conditions) of user 106 from an electronic medical record (EMR) system, a health research platform (such as the PatientsLikeMe™ database), claims data, and so on. In some examples, recommendation system 110 may obtain data regarding the health conditions of user 106 based on data in claims database 216.

In some examples, supplemental data 310 may include data regarding pharmacy products associated with user 106. Example types of pharmacy products may include drugs, biologics, adaptive medical devices, supplements, and so on that may be prescribed or non-prescribed. Recommendation system 110 may obtain the data regarding the pharmacy products from electronic pharmacy records, EMR systems, health research platforms, and other data sources. In some examples, recommendation system 110 may obtain the data regarding the pharmacy products from claims database 216. For instance, claims database 216 may include data regarding health insurance claims (including pharmacy benefit claims) related to user 106. Recommendation system 110 may process the data in claims database 216 to determine which conditions user 106 has been treated for, what pharmacy products user 106 are associated with user 106, and/or other data.

In some examples where recommendation system 110 obtains data regarding the health conditions of user 106 and/or pharmacy product associated with user 106 from data sources such as EMR systems, claims database 216, etc., recommendation system 110 may filter older or non-current health conditions or pharmacy products from supplemental data 310 so that supplemental data is more likely to reflect current health conditions and/or pharmacy products associated with user 106.

Dense neural network 306 may be a fully connected neural network. An input layer of dense neural network may include an input neuron for each piece of data generated input data merging layer 304. An output layer of dense neural network 306 may include a neuron for each healthcare provider in a plurality of healthcare providers. The output neuron for a healthcare provider outputs a score for the healthcare provider. Dense neural network 306 may include one or more hidden layers between the input layer and the output layer. In some examples, the activation function for the hidden layers in the dense neural network 306 use Rectified Linear Unit (ReLU) activation functions and the output layer uses a Softmax activation function. The number of neurons in the hidden layer(s) of dense neural network 306 is between the number of input neurons and number of output neurons. Between the input, hidden and output layers, dropout layers are used to reduce overfitting. Categorical cross-entropy is used as the loss function for the output layer of the dense neural network 306.

Figure 4:
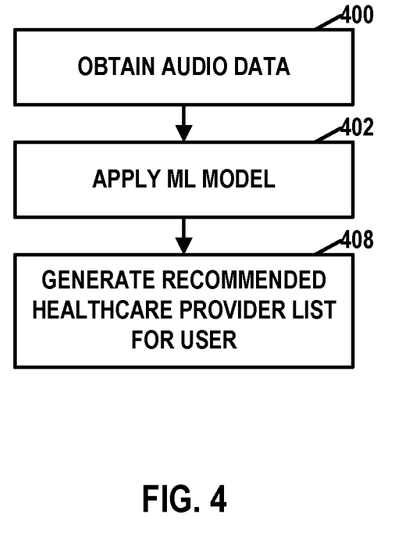
FIG. 4 is a flowchart illustrating an example method in accordance with one or more techniques of this disclosure.

FIG. 4 is a flowchart illustrating an example operation in accordance with one or more techniques of this disclosure. In the example of FIG. 4, computing system 102 may obtain audio data representing sounds generated by user 106 (400). For instance, in the example of FIG. 1, recommendation system 110 of computing system 102 may obtain the audio data via IVS 108.

Furthermore, in the example of FIG. 4, computing system 102 (e.g., recommendation system 110 of computing system 102) may apply ML model 112 (402). ML model 112 generates output data based at least in part on non-semantic content of the audio data. When computing system 102 applies ML model 112, computing system 102 may provide input data to ML model 112 as process the input data forward through the networks (and layers thereof) until an output layer of ML model 112 generates the output data. As part of applying ML model 112, computing system 102 may extract non-semantic content from the audio data. The non-semantic content of the audio data may include the vocal biomarkers. As part of applying ML model 112, computing system 102 may generate the output data based at least in part on the non-semantic content. Furthermore, in some examples, computing system 102 may generate the output based on the non-semantic content and supplemental data, e.g., as described elsewhere in this disclosure. The supplemental data may include data indicating health conditions of user 106 and other information. In some examples, computing system 102 may determine the health conditions of user 106 based on prior health insurance claims of user 106.

Computing system 102 may generate, based on the output data generated by ML model 112, a recommended healthcare provider list for user 106 (404). The recommended healthcare provider list for user 106 includes one or more healthcare providers recommended for user 106. For example, as part of generating the recommended healthcare provider list, computing system 102 may filter the recommended healthcare provider list based on one or more exclusion criteria. Such exclusion criteria may include one or more of postal codes of the healthcare providers, availability of transportation for user 106 to the healthcare providers, required minimum ratings of the healthcare providers, or other factors.

For processes, apparatuses, and other examples or illustrations described herein, including in any flowcharts or flow diagrams, certain operations, acts, steps, or events included in any of the techniques described herein can be performed in a different sequence, may be added, merged, or left out altogether (e.g., not all described acts or events are necessary for the practice of the techniques). Moreover, in certain examples, operations, acts, steps, or events may be performed concurrently, e.g., through multi-threaded processing, interrupt processing, or multiple processors, rather than sequentially. Further certain operations, acts, steps, or events may be performed automatically even if not specifically identified as being performed automatically. Also, certain operations, acts, steps, or events described as being performed automatically may be alternatively not performed automatically, but rather, such operations, acts, steps, or events may be, in some examples, performed in response to input or another event.

Further, certain operations, techniques, features, and/or functions may be described herein as being performed by specific components, devices, and/or modules. In other examples, such operations, techniques, features, and/or functions may be performed by different components, devices, or modules. Accordingly, some operations, techniques, features, and/or functions that may be described herein as being attributed to one or more components, devices, or modules may, in other examples, be attributed to other components, devices, and/or modules, even if not specifically described herein in such a manner.

In one or more examples, the functions described may be implemented in hardware, software, firmware, or any combination thereof. If implemented in software, the functions may be stored on or transmitted over a computer-readable medium as one or more instructions or code and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable medium.

By way of example, and not limitation, such computer-readable storage media can include RAM, ROM, EEPROM, CD-ROM, or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transitory media, but are instead directed to non-transitory, tangible storage media. Disk and disc, as used herein, includes compact disc (CD), laser disc, optical disc, digital versatile disc (DVD), and Blu-ray disc, where disks usually reproduce data magnetically, while discs reproduce data optically with lasers. Combinations of the above should also be included within the scope of computer-readable media.

Instructions may be executed by one or more processors, such as one or more DSPs, general purpose microprocessors, ASICs, FPGAs, or other equivalent integrated or discrete logic circuitry, as well as any combination of such components. Accordingly, the term "processor," as used herein, may refer to any of the foregoing structures or any other structure suitable for implementation of the techniques described herein. In addition, in some aspects, the functionality described herein may be provided within dedicated hardware and/or software modules. Also, the techniques could be fully implemented in one or more circuits or logic elements.

The techniques of this disclosure may be implemented in a wide variety of devices or apparatuses, including a wireless communication device or wireless handset, a microprocessor, an integrated circuit (IC) or a set of ICs (e.g., a chip set). Various components, modules, or units are described in this disclosure to emphasize functional aspects of devices configured to perform the disclosed techniques, but do not necessarily require realization by different hardware units. Rather, as described above, various units may be combined in a hardware unit or provided by a collection of interoperative hardware units, including one or more processors as described above, in conjunction with suitable software and/or firmware.

What is claimed is:

1. A computer-implemented method comprising:
   obtaining, by one or more processors, (1) audio data representing sounds generated by a user and (2) supplemental data associated with the user, wherein the audio data comprises one or more frames of audio data;
   applying, by the one or more processors, a fast Fourier transform (FFT) to each frame of the one or more frames of the audio data to determine a corresponding array of transform coefficients in a frequency domain;
   applying, by the one or more processors and for each frame of the one or more frames, a convolutional neural network (CNN) to the corresponding array of transform coefficients to generate a corresponding intermediate output, wherein the CNN has a same number of dimensions as the corresponding array of transform coefficients;
   applying, by the one or more processors, a recurrent neural network (RNN) to each corresponding intermediate output to extract non-semantic content from the audio data;
   merging, by the one or more processors, the non-semantic content with the supplemental data to generate input data;
   applying, by the one or more processors, a dense neural network to the input data to generate one or more scores associated with one or more healthcare providers; and
   generating, by the one or more processors and based on the one or more scores, a ranked healthcare provider list,
   wherein one or more of the CNN, the RNN, or the dense neural network is trained based on training data that includes health insurance claims data that indicates a healthcare provider from the healthcare provider list.

2. The computer-implemented method of claim 1, wherein obtaining the audio data comprises generating, by a smart speaker, the audio data representing the sounds generated by the user.

3. The computer-implemented method of claim 1, wherein the supplemental data includes data indicating health conditions of the user.

4. The computer-implemented method of claim 3, further comprising determining the health conditions of the user based on prior health insurance claims of the user.

5. The computer-implemented method of claim 1, wherein generating the healthcare provider list comprises:
   filtering the healthcare provider list based on one or more exclusion criteria.

6. The computer-implemented method of claim 5, wherein the one or more exclusion criteria include one or more of: availability of transportation for the user to the one or more healthcare providers, or required minimum ratings of the one or more healthcare providers.

7. The computer-implemented method of claim 1, wherein the supplemental data includes at least one of:
   typical wait times for the one or more healthcare providers,
   demographic data regarding the user, or
   pharmacy products associated with the user.

8. The computer-implemented method of claim 1, wherein generating the ranked healthcare provider list comprises generating the healthcare provider list based on a plurality of components, the plurality of components comprising the one or more scores and at least one of:

a number of years of experience of each healthcare provider of the one or more healthcare providers;
a healthcare provider rating for each healthcare provider of the one or more healthcare providers;
a distance between the user and each healthcare provider of the one or more healthcare providers; or
an amount of compliance between preferences of the user and each healthcare provider of the one or more healthcare providers.

9. A computing system comprising:
one or more processors implemented in circuitry, the one or more processors configured to:
obtain (1) audio data representing sounds generated by a user and (2) supplemental data associated with the user, wherein the audio data comprises one or more frames of audio data;
apply a fast Fourier transform (FFT) to each frame of the one or more frames of the audio data to determine a corresponding array of transform coefficients in a frequency domain;
apply, for each frame of the one or more frames, a convolutional neural network (CNN) to the corresponding array of transform coefficients for the frame to generate a corresponding intermediate output, wherein the CNN has a same number of dimensions as the array of transform coefficients;
apply a recurrent neural network (RNN) to each corresponding intermediate output to extract the non-semantic content from the audio data;
merge the non-semantic content with the supplemental data to generate input data;
apply a dense neural network to the input data to generate one or more scores for one or more healthcare providers; and
generate, based on the one or more scores, a ranked healthcare provider list; and
a communication unit configured to send the ranked healthcare provider list,
wherein one or more of the CNN, the RNN, or the dense neural network is trained based on training data that includes health insurance claims data that indicates a healthcare provider from the healthcare provider list.

10. The computing system of claim 9, wherein the computing system includes a smart speaker configured to generate the audio data.

11. The computing system of claim 9, wherein the supplemental data includes data indicating health conditions of the user.

12. The computing system of claim 11, wherein the one or more processors are further configured to determine the health conditions of the user based on prior health insurance claims of the user.

13. The computing system of claim 9, wherein the one or more processors are configured such that, as part of generating the healthcare provider list, the one or more processors filter the healthcare provider list based on one or more exclusion criteria.

14. The computing system of claim 13, wherein the one or more exclusion criteria include one or more of: availability of transportation for the user to the one or more healthcare providers, or required minimum ratings of the one or more healthcare providers.

15. The computing system of claim 9, wherein to generate the ranked healthcare provider list, the one or more processors are configured to:
generate the ranked healthcare provider list based on a plurality of components, the plurality of components comprising the one or more scores and at least one of:
a number of years of experience of each healthcare provider of the one or more healthcare providers;
a healthcare provider rating for each healthcare provider of the one or more healthcare providers;
a distance between the user and each healthcare provider of the one or more healthcare providers; or
an amount of compliance between preferences of the user and each healthcare provider of the one or more healthcare providers.

16. One or more non-transitory computer-readable storage media comprising instructions that, when executed by one or more processors, cause the one or more processors to:
obtain (1) audio data representing sounds generated by a user and (2) supplemental data associated with the user, wherein the audio data comprises one or more frames of audio data;
apply a fast Fourier transform (FFT) to each frame of the one or more frames of the audio data to determine a corresponding array of transform coefficients;
apply, for each frame of the one or more frames, a convolutional neural network (CNN) to the corresponding array of transform coefficients to generate a corresponding intermediate output, wherein the CNN has a same number of dimensions as the array of transform coefficients;
apply a recurrent neural network (RNN) to each corresponding intermediate output to extract non-semantic content from the audio data;
merge the non-semantic content with the supplemental data to generate input data; and
apply a dense neural network to the input data to generate one or more scores for one or more healthcare providers; and
generate, based on the one or more scores, a ranked healthcare provider list,
wherein one or more of the CNN, the RNN, or the dense neural network is trained based on training data that includes health insurance claims data that indicates a healthcare provider from the healthcare provider list.

* * * * *